United States Patent [19]

Wasfi

[11] Patent Number: 5,041,576
[45] Date of Patent: Aug. 20, 1991

[54] ANTIMONY OXO-METALATE COMPLEXES

[76] Inventor: Sadio H. Wasfi, 286 Pine Valley Rd., Dover, Del. 19901

[21] Appl. No.: 615,492

[22] Filed: Nov. 19, 1990

Related U.S. Application Data

[63] Continuation-in-part of Ser. No. 447,061, Dec. 7, 1989.

[51] Int. Cl.$^5$ .......................... C07F 9/90; C07F 11/00; A01N 55/02; A61K 31/28
[52] U.S. Cl. .......................................... 556/30; 556/32; 556/36; 556/70; 514/885
[58] Field of Search ....................... 556/28, 30, 32, 36, 556/64, 70; 514/6, 184, 492, 503, 934, 885

[56] References Cited

U.S. PATENT DOCUMENTS

| | | | |
|---|---|---|---|
| 3,504,005 | 3/1970 | Moedritzer et al. | 556/64 X |
| 3,778,385 | 12/1973 | Zuech | 556/28 X |
| 3,944,586 | 3/1976 | Knowles | 556/36 X |
| 4,310,469 | 1/1982 | Crivello | 556/64 |
| 4,425,278 | 1/1984 | Wirth et al. | 556/28 X |
| 4,544,759 | 10/1985 | Hlavka et al. | 556/36 |
| 4,562,276 | 12/1985 | Venturello et al. | 556/30 X |
| 4,798,857 | 1/1989 | Bertelli et al. | 556/36 X |
| 4,904,808 | 2/1990 | Devon et al. | 556/30 X |
| 4,921,985 | 5/1990 | Besecker et al. | 556/64 X |

Primary Examiner—Arthur C. Prescott
Attorney, Agent, or Firm—John C. Andrade

[57] ABSTRACT

Antimony oxo-metalate complexes having anti-viral activity are disclosed. The disclosed complexes are organic derivatives of tungstoantimonate or molybdoantimonate.

20 Claims, 2 Drawing Sheets

ANTIMONY OXO-METALATE COMPLEXES

This application is a continuation in part of application Ser. No. 447,061 filed Dec. 7, 1989, now abandoned.

BACKGROUND

This application relates to antimony oxometalate complexes that have activity on viruses. Heteropoly oxo-metalate complexes have been widely used as catalysts. There have been some limited studies into antiviral activity of some antimony oxo-metalate complexes. Some heteropoly anions (HPA) have been studied and a few of them like HPA 23 have been shown to have some effect as antiviral agents. The disadvantages of HPA 23 are its relatively high molecular weight and high toxicity.

Acquired Immune Deficiency Syndrome (AIDS) is a condition in which an acquired deficiency of certain leukocytes results in a variety of infections, some forms of cancer and nervous system degeneration caused by a virus which infects T cells and is transmitted in body fluids.

There are two related but distinct viruses that can cause AIDS. They are presently designated HIV 1 HIV 1 and HIV 2. The genomes of HIV-1 and HIV-2 are only about 50% homologous at the nucletide level, but the two viruses contain the same number of complement genes and appear to attack and kill the same human cells.

The two immunodeficiency viruses are retroviruses in which the genetic material is RNA rather than DNA. These viruses carry with them an enzyme called *Reverse.Transcriptase*, a polymerase that catalyzes transcription of viral RNA to double helical DNA. This viral DNA may exist in an unintegrated form in the infected cell, or a copy called proviral DNA may be integrated into the genome of the infected cells.

Proviral HIV may persist in a lateral form or encode messenger RNA and genomic RNA to result in formation of new virus particles. HIV also causes significant damage beyond the immune system, mild to severe neurological systems are often manifested as a progressive dementia. The symptoms are referred to as AIDS encephalopathy and sometimes occur before the patients develop AIDS itself.

SUMMARY OF THE INVENTION

Certain antimony oxo-metalate complexes made from a combination of stibonic acid and molybdate or tungstate have now been discovered. These complexes have been tested for and shown indications of anti-viral activity and one of the complexes has shown substantial anti-viral activity on HIV.

The process for making antimony oxometalate complexes comprises:

(a) mixing a simple metalate and stibonic acid dissolved in water and adjusting the pH of the resulting solution to 5–6.5;

(b) boiling said solution and allowing it to cool;

(c) adding a cation, preferably guanidinium hydrochloride; and preferably filtering to remove precipitate and depositing of crystals from the standing solution.

The simple metalate is preferably $Na_2WO_4H_2O$ or $Na_2MoO_4$.

The antimony oxo-metalate complex formed by such process where $Na_2WO_4H_3O$ is used is believed to have the formula $(A)_x[(C_6H_5Sb)_2W_nO_m]^{-x}$ where n has a value of 5–8, m has a value of 24–32, x has a value of 4–8 and A is a cation, and preferably n=6, m=24 and x=6 and more preferably n=8, m=32 and x=6 and the cation is guanidinium.

The antimony oxo-metalate complex formed by such process where $Na_2MoO_4$ is used is believed to have the general formula $(D)_y(C_6H_5Sb)_bMo_cO_dH_e$, where y has a value of 2–5, b has a value of 1–2, c has a value of 4–6, d has a value of 15–24, e has a value of 1–2 and D is a cation, preferably guanadinium, and preferably a=2, b=1, c=4, d=15, and e=1.

Precaution must be exercized in the preparation and handling of stibonic acid because all antimony compounds are highly toxic.

EXAMPLE 1

Figure 1:
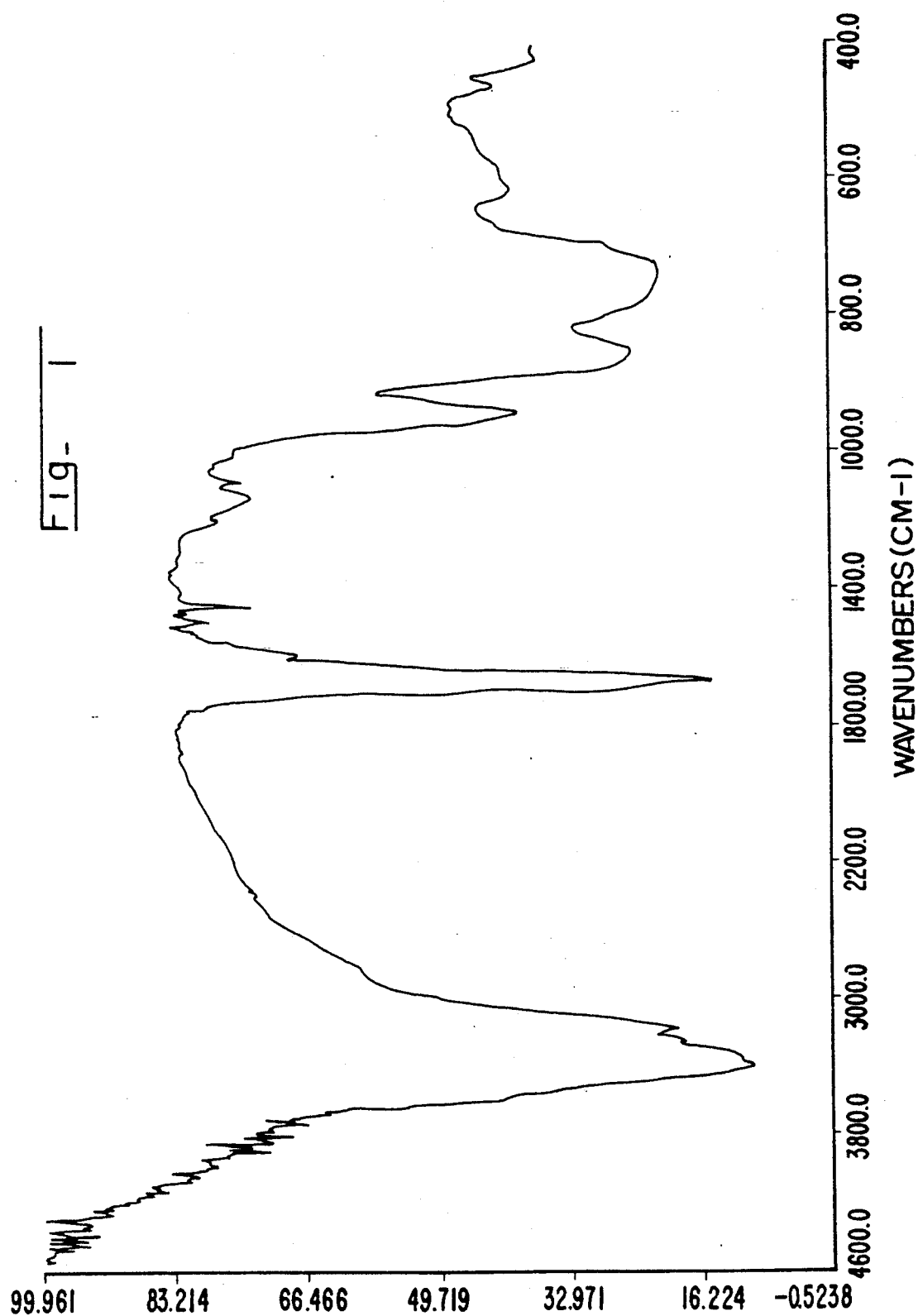
FIG. 1 is an IR Spectrum readont of an analyzed sample of a compound within the scope of this invention.

Stibonic acid ($C_6H_5SbO_3H_2$) was prepared as follows:

To a mixture of 500 ml 2-propanol and 20 g (0.2 mol) $H_2SO_4$ in a 2 liter beaker at 0° C. was added 18.6 ml (0.2 mol) aniline, dropwise. The mixture became thick and white. Then 55.6 g (0.2 mol) of finely ground $SbCl_3$ was added portionwise to the mixture. The mixture was kept at 0° C. and stirred 20 minutes to effect dissolution. The diazotization was effected by the addition of 14.0 g (0.2 ml) of $NaNO_2$ dissolved in 20 ml $H_2O$ (exothermic). The reaction was stirred for ½ hour at 0° C. at which time 4.0 g cuprous bromide was added. The ice bath was then removed and the reaction was allowed to warm to room temperature. Nitrogen was evolved as the mixture warmed. To facilitate the removal of 2-propanol, the mixture was heated to 60° C. while passing a steady stream of air over the reaction. (Steam distillation was used in the original procedure to remove the alcohol.) Then the crude stibonic acid was poured into iced water and filtered. The solids were collected, air dried and dissolved in 200 ml concentrated HCl, then 100 ml pyridinium hydrochloride was added. (The latter was made by adding 20 ml of pyridine to 80 ml of concentrated HCl.) The mixture was cooled to room temperature and filtered. The solids were collected and dissolved in four liters of dilute sodium carbonate. 5.0 g of activated charcoal was added and again filtered. The free stibonic acid was obtained by acidifying the filtrate with 10% HCl. The stibonic acid was immediately filtered and air dried to avoid disproportionation upon standing in water.

EXAMPLE 2

The organic derivative of Tungsto-Antimonate was prepared as follows:

A mixture of 8.0 g (0.024 mol) $Na_2WO_4H_2O$ and 2.0 g (0.008mol) of $C_6H_5SbO_3H_2$ was dissolved in water and the pH of the resulting solution was then adjusted to 6.5 with a 50/50 solution of sulfuric acid. The solution was brought to a boil and allowed to cool, and a solution of 2.0 g guanidinium hydrochloride in 10 ml $H_2O$ was added dropwise while stirring. After filtration, to remove the precipitate, the solution was allowed to stand to deposit crystals of the organic derivative of Tungsto-Antimonate.

The I.R. Spectrum of the analyzed sample is shown in FIG. 1 and is characterized by an absorption around 920 $cm^{-1}$ with strong intensity followed by more intense absorption around 853 $cm^{-1}$, and this is followed by broad absorption around 750 cm, followed by several very weak absorptions.

Figure 2:
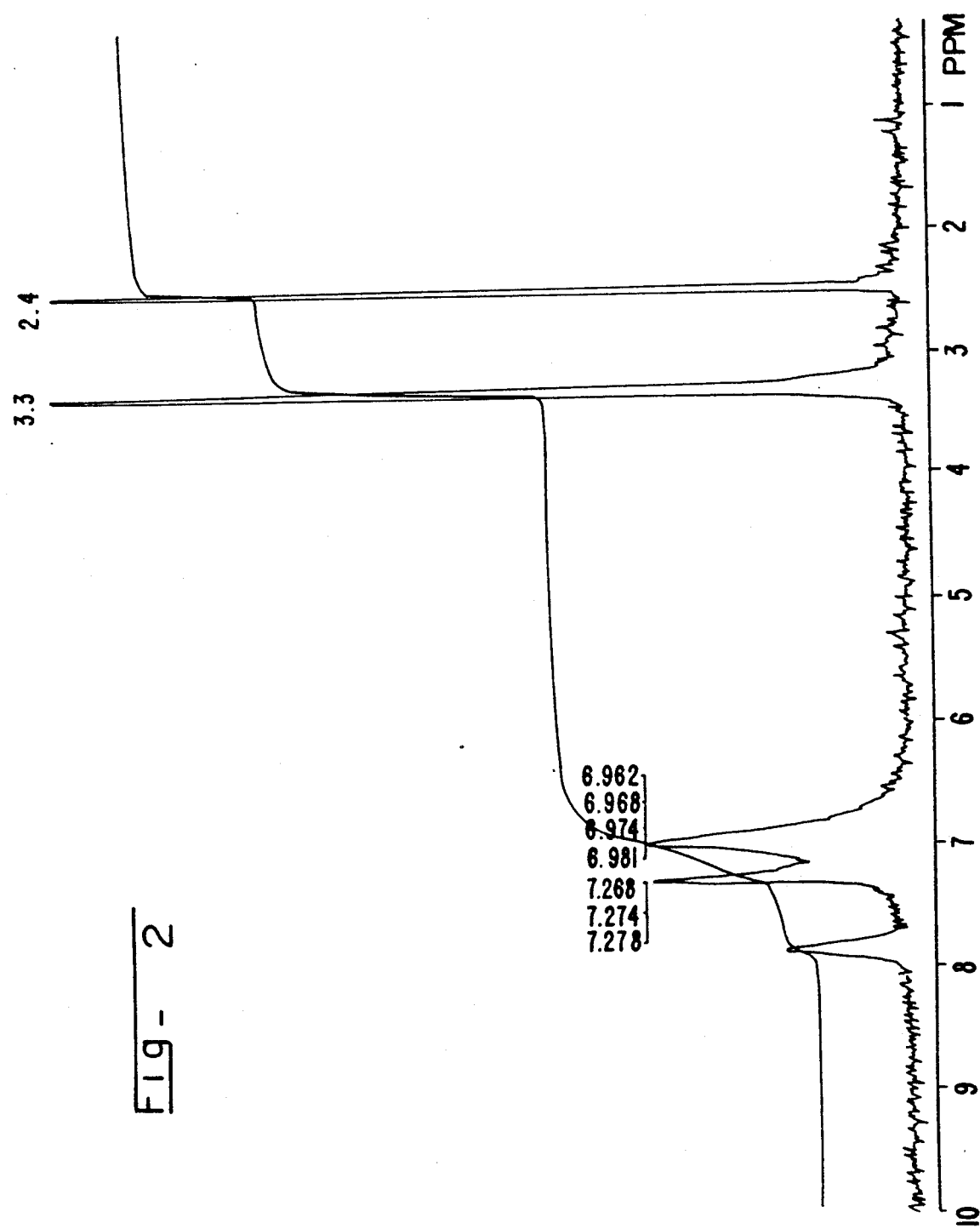
FIG. 2 is a proton NMJR readont of an analyzed sample of a compound within the scope of this invention.

The proton NMR of the analyzed sample at 90 MHZ as shown in FIG. 2 and shows the phenyl protons as unresolved doublets with the same intensity centered at 6-97 ppm and 7.26 ppm respectively. This doublets is followed by a singlet centered at 7.75 ppm. The phenyl proton in the uncomplexed stibonic acid appear as unresolved multiplets centered around 7.4.ppm.

EXAMPLE 3

The organic derivative of molybdoantimonate was prepared as follows:

A mixture of 5.8g $Na_2MO_4$ (0.024 mol) and 2.0g $C_6H_5SbO_3H_2$ (0.008 mol) was dissolved in 75 ml $H_2O$ and the pH of the resulting solution was adjusted to 6.5 with a 50/50 $H_2SO_4$ solution. The solution was brought to a boil and allowed to cool, and a solution of 2.0g of guanidinium hydrochloride in 10 ml $H_2O$ was added dropwise while stirring. After filtering to remove the precipitate, the solution was allowed to stand to deposit crystals of the organic derivative of molybdoantimonate.

The proton NMR of the organic derivitive of molybdoantimonate has a strong, sharp singlet around 7.1 ppm which means all the phenyl protons in the complex appear to be magnetically equivalent, in contrast to the phenyl protons in the uncomplexed stibonic acid appear as unresolved multiplets centered around 7.4 ppm.

The infrared spectrum of the compound is identified by an intense absorption around 900 $cm^{-1}$ usually assigned as due to Mo-0 stretching, followed by two weak absorptions around 820 and 860 $cm's^{-1}$. These two absorptions are followed by a split absorption with moderate intensity between 750-700 $cm^{-1}$. This is followed by four weak absorptions at 620, 580, 540 and 470 $cm's^{-1}$ respectively.

The carbon thirteen NMR of the compound shows three singlets in decreasing intensities from 118.31 ppm, 93-61 ppm, and 88.36 ppm from the reference DMSO at 39.5 ppm. These peaks are tentatively assigned as: the peak at 118.31 ppm is the meta-para carbons unresolved. The absorption at 93.6 ppm is due to the ortho carbons and finally the peak at 88.36 ppm is the carbon which is bonded to the antimony.

EXAMPLE 4

The organic derivative of the Tungsto-Antimonate, prepared according to Example 2 believed to be of the formula $(CN_3H_6)_6(C_6H_5Sb)_2W_8O_{32}.3H_2O$ was tested for activity against HIV. It was found to have activity against HIV with low cytotoxic effect.

The procedure used below is the National Cancer Institute's test for agents active against HIV and is designed to detect agents acting at any stage of the virus reproductive cycle. The assay basically involves the killing of T4 lympocytes by HIV. Small amounts of HIV are added to cells, and a complete cycle of virus reproduction is necessary to obtain the required cell killing. Agents that interact with virions, cells, or virus gene products to interfere with viral activities will protect cells from cytolysis. The system is generally designed to detect anti-HIV activity. All tests are compared with a positive (AZT-treated) control done at the same time under identical conditions.

The Procedure:

1. Candidate agent is dissolved in dimethyl sulfoxide (unless otherwise instructed), then diluted 1:200 in cell culture medium. Further dilutions (half-$log_{10}$) are prepared before adding to 96-well microtiter plates.

2. T4 lymphocytes (CEM cell line) are exposed to HIV at a virus-to-cell ratio of approximately 0.05 and are plated along with noninfected control cells into drug-containing wells or wells with medium alone.

3. Cultures are incubated at 37° in a 5% carbon dioxide atmosphere for 6 days.

4. The tetrazolium salt, XTT, is added to all wells, and cultures are incubated to allow formazan color development by viable cells.

5. Individual wells are analyzed spectrophotometrically to quantitate formazan production and, in addition, are viewed microscopically for detection of viable cells and confirmation of protective activity.

6. Drug-treated virus-infected cells are compared with drug-treated noninfected cells and with other appropriate controls (untreated infected and untreated noninfected cells, drug-containing wells without cells, etc.) on the same plate.

7. Data are reviewed in comparison with other tests done at the same time, and a determination about activity is made.

In table 1-6 below, the Infected Response Column indicates the percentage of surviving HIV-infected cells treated at the indicated concentration relative to uninfected, "untreated" controls. This column expresses the in vitro anti-HIV activity of the sample. The Uninfected Response column indicates the percentage of surviving uninfected cells treated with the sample relative to the same uninfected, untreated controls. The column expresses the in vitro growth inhibitory properties of the sample. The viral cytopathic effect (VCE) in this particular experiment is the extent of destruction of cells by the virus in the absence of treatment and is used as a quality control parameter. Survival values of this parameter less than 50% are considered acceptable in this protocol. Approximate values for 50% effective concentration ($EC_{50}$), 50% inhibitory concentration ($IC_{50}$) and Therapeutic Indeix (TI=$IC_{50}/EC_{50}$) have been calculated for each test and are provided below. The determination of the activity of the compound is given in the lower left-hand corner of the table.

TABLE 1

| Dose (ug/ml) | Infected Response Percent of Control | Uninfected Response Percent of Control |
| --- | --- | --- |
| $7.94 \times 10^{-2}$ | 4.98 | 121.71 |
| $2.51 \times 10^{-1}$ | 5.49 | 60.97 |
| $7.93 \times 10^{-1}$ | 10.86 | 30.30 |
| $2.50 \times 10^0$ | 18.06 | 126.87 |
| $7.92 \times 10^0$ | 15.48 | 70.34 |
| $2.50 \times 10^{+1}$ | 31.36 | 112.41 |
| $7.91 \times 10^{+1}$ | 91.81 | 97.62 |
| $2.50 \times 10^{+2}$ | 80.22 | 81.31 |

| SUMMARY | VCE = 10% |
| --- | --- |
| Index | Concentration |
| IC50 (ug/ml) | $2.24 \times 10^1$ |
| EC50 (ug/ml) | |
| TI50 (IC/EC) | |
| Conclusion: | ACTIVE |

TABLE 2

| Dose (ug/ml) | Infected Response Percent of Control | Uninfected Response Percent of Control |
|---|---|---|
| $7.94 \times 10^{-2}$ | 23.09 | 120.93 |
| $2.51 \times 10^{-1}$ | 22.26 | 112.36 |
| $7.93 \times 10^{-1}$ | 29.33 | 108.00 |
| $2.50 \times 10^{0}$ | 27.00 | 61.37 |
| $7.92 \times 10^{0}$ | 23.92 | 145.75 |
| $2.50 \times 10^{+1}$ | 58.13 | 131.46 |
| $7.91 \times 10^{+1}$ | 178.99 | 222.76 |
| $2.50 \times 10^{+2}$ | 32.64 | 78.52 |

| SUMMARY | VCE = 23% |
|---|---|
| Index | Concentration |
| IC50 (ug/ml) | $>2.50 \times 10^{2}$ |
| EC50 (ug/ml) | $1.90 \times 10^{1}$ |
| T150 (IC/EC) | $>1.31 \times 10^{1}$ |
| Conclusion: | ACTIVE |

TABLE 3

| Dose (ug/ml) | Infected Response Percent of Control | Uninfected Response Percent of Control |
|---|---|---|
| $7.94 \times 10^{-2}$ | 13.77 | 106.25 |
| $2.51 \times 10^{-1}$ | 21.55 | 98.91 |
| $7.93 \times 10^{-1}$ | 16.41 | 104.90 |
| $2.50 \times 10^{0}$ | 30.69 | 114.87 |
| $7.92 \times 10^{0}$ | 45.86 | 112.08 |
| $2.50 \times 10^{+1}$ | 76.40 | 107.37 |
| $7.91 \times 10^{+1}$ | 88.09 | 96.43 |
| $2.50 \times 10^{+2}$ | 79.71 | 88.21 |

| SUMMARY | VCE = 18% |
|---|---|
| Index | Concentration |
| IC50 (ug/ml) | $>2.50 \times 10^{2}$ |
| EC50 (ug/ml) | $9.25 \times 10^{0}$ |
| T150 (IC/EC) | $>2.70 \times 10^{1}$ |
| Conclusion: | ACTIVE |

TABLE 4

| Dose (ug/ml) | Infected Response Percent of Control | Uninfected Response Percent of Control |
|---|---|---|
| $7.94 \times 10^{-2}$ | 4.27 | 93.52 |
| $2.51 \times 10^{-1}$ | 4.57 | 91.73 |
| $7.93 \times 10^{-1}$ | 3.43 | 92.63 |
| $2.50 \times 10^{0}$ | 4.03 | 97.10 |
| $7.92 \times 10^{0}$ | 5.17 | 101.18 |
| $2.50 \times 10^{+1}$ | 63.06 | 90.74 |
| $7.91 \times 10^{+1}$ | 80.26 | 84.88 |
| $2.50 \times 10^{+2}$ | 40.45 | 29.52 |

| SUMMARY | VCE = 4% |
|---|---|
| Index | Concentration |
| IC50 (ug/ml) | $1.63 \times 10^{2}$ |
| EC50 (ug/ml) | $3.13 \times 10^{1}$ |
| T150 (IC/EC) | $5.22 \times 10^{0}$ |
| Conclusion: | ACTIVE |

TABLE 5

| Dose (Molar) | Infected Response Percent of Control | Uninfected Response Percent of Control |
|---|---|---|
| $3.60 \times 10^{-8}$ | 1.83 | 93.04 |
| $1.14 \times 10^{-7}$ | 2.40 | 93.04 |
| $3.60 \times 10^{-7}$ | 4.44 | 91.79 |
| $1.13 \times 10^{-6}$ | 14.20 | 94.40 |
| $3.59 \times 10^{-6}$ | 4.91 | 80.93 |
| $1.13 \times 10^{-5}$ | 56.96 | 41.77 |
| $3.59 \times 10^{-5}$ | 52.84 | 34.25 |
| $1.13 \times 10^{-4}$ | 20.88 | 8.88 |

| SUMMARY | VCE = 4% |
|---|---|
| Index | Concentration |
| IC50 (Molar) | $8.88 \times 10^{-6}$ |
| EC50 (Molar) | $9.69 \times 10^{-6}$ |
| T150 (IC/EC) | $9.16 \times 10^{1}$ |

TABLE 5-continued

| Conclusion: | ACTIVE |
|---|---|

TABLE 6

| Dose (Molar) | Infected Response Percent of Control | Uninfected Response Percent of Control |
|---|---|---|
| $3.60 \times 10^{-8}$ | 3.49 | 106.38 |
| $1.14 \times 10^{-7}$ | 3.23 | 105.23 |
| $3.60 \times 10^{-7}$ | 4.38 | 105.75 |
| $1.13 \times 10^{-6}$ | 12.46 | 107.42 |
| $3.59 \times 10^{-6}$ | 2.61 | 97.83 |
| $1.13 \times 10^{-5}$ | 63.25 | 44.64 |
| $3.59 \times 10^{-5}$ | 55.07 | 37.23 |
| $1.13 \times 10^{-4}$ | 18.56 | 12.10 |

| SUMMARY | VCE = 2% |
|---|---|
| Index | Concentration |
| IC50 (Molar) | $1.01 \times 10^{-5}$ |
| EC50 (Molar) | $8.80 \times 10^{-6}$ |
| T150 (IC/EC) | $1.14 \times 10^{0}$ |
| Conclusion: | ACTIVE |

EXAMPLE 5

The molecular weight of the made under Example 2 was determined by. The molecular ion regions of the FAB mass were recorded. Because of the number of elements present that have multiple isotopes, recording mass spectra at unit resolution would the signals over so many peaks that sensitivity would be significantly reduced. The spectra were, therefore, recorded at low (1:500) resolution. The peak centers represent the average mass of the cluster, and were used to determine the value reported which is in agreement with the formulation of the compound. Although the instrument's sensitivity is usually lower in the negative ion mode than in the positive mode, the negative ion signal was two to three times that obtained in the positive ion mode. This observation is consistent with the anionic compound's strong preference for carrying a negative charge.

TABLE 7

ANALYTICAL RESULTS OF $(CH_3H_6)_6(C_6H_5Sb)_2W_8O_{32}\cdot 3H_2O$

| Element | Found | Calculated from Formula |
|---|---|---|
| C | 8.95% | 7.87% |
| H | 2.07% | 1.75% |
| N | 8.35% | 9.19% |
| Sb | 10.38% | 8.83% |
| W | 45.57% | 53.60% |

The molecular weight of the anhydrous compound is 2742.
The analyzed sample might contain a small amount of unreacted $C_6H_5SbO_3$.

We claim:

1. A compound having an organic. derivative of a Tungsto- Antimonate anion and having the general formula $(A)_x[(C_6H_5Sb)_2W_nO_m]^{-x}$ where n has a value of 5–8, m has a value of 24–32, and x has a value of 4–8 and A is a cation.

2. The compound of claim 1 wherein n=6, m=24 and x=6.

3. The compound of claim 1 wherein n=8, m=32 and x=6.

4. The compound of claim 3 wherein the cation is guanadinium.

5. The compound of claim 4 having the IR spectrum shown in FIG. 1.

6. The compound of claim 3 wherein the anion itself has the proton NMR shown in FIG. 2.

7. The process of making an antimony oxo-metalate complex comprising:
   (a) mixing simple metalate and stibonic acid dissolved in water and adjusting the pH of the resulting solution to 5-6.5;
   (b) boiling said solution and allowing it to cool; and
   (c) adding a cation;
8. The process of claim 7 wherein the simple metalate is $Na_2WO_4H_2O$.
9. The process of claim 7 wherein the simple metalate is $Na_2MoO_4$.
10. The process of claim 8 wherein the cation is guanidinium hydrochloride.
11. The process of claim 9 wherein the cation is guanidinium hydrochloride.
12. The process of claim 10 further comprising filtering to remove precipitate and depositing of crystals from the standing solution.
13. An organic derivative of Molybdoantimonate having the general formula $(D)_y(C_6H_5Sb)_bMo_cO_dH_e$ where y has a value of 2-5, b has a value of 1-2, c has a value of 4-6, d has a value of 15-24, e has a value of 1-2 and D is a cation.
14. The organic derivative of claim 13 wherein the cation is guanidinium.
15. The compound of claim 14 wherein $a=2$, $b=1$, $c=4$, $d=15$ and $e=1$.
16. A method of treating viruses by exposing said viruses to the anion of claim 1.
17. The method of claim 16 wherein the virus is HIV.
18. A method of treating HIV by exposing the HIV virus to the compound of claim 5.
19. An antimony oxo-metalate complex made by the process of claim 7.
20. An antimony oxo-metalate complex made by the process of claim 10.

* * * * *

UNITED STATES PATENT AND TRADEMARK OFFICE
CERTIFICATE OF CORRECTION

PATENT NO. : 5,041,576  
DATED : August 20, 1991  
INVENTOR(S) : Wasfi

It is certified that error appears in the above-indentified patent and that said Letters Patent is hereby corrected as shown below:

Title page, item [76], Sadio H. Wasfi, should read --Sadiq H. Wasfi--.

Col. 1, line 68, "$Na_2WO_4H_3O$" should read --$Na_2WO_4H_2O$--.

Col. 4, line 14, "37°" should be followed by "C".

Col. 4, lines 64-65, "2.24 x 10' " should be moved from line 64 to line 65 opposite "EC50 (ug/ml)".

Col. 6, line 25, after "the" insert --compound--.

Col. 6, line 26, after "by" insert --FABMS--.

Col. 6, line 27, after "mass" insert --spectra--.

Col. 6, line 28, after "recording" insert --of--.

Col. 6, line 29, after "would" insert --distribute--.

Col. 6, line 43, the formula "$(CH_3H_6)_6(C_6H_5Sb)_2W_8O_{32} \cdot 3H_2O$" should read --$(CN_3H_6)_6(C_6H_5Sb)_2W_8O_{32} \cdot 3H_2O$--.

UNITED STATES PATENT AND TRADEMARK OFFICE
CERTIFICATE OF CORRECTION

PATENT NO. : 5,041,576
DATED : August 20, 1991
INVENTOR(S) : Wasfi

It is certified that error appears in the above-indentified patent and that said Letters Patent is hereby corrected as shown below:

Col. 6, line 64, "guanadinium" should read --guanidinium--.

Signed and Sealed this

Eighth Day of June, 1993

Attest:

MICHAEL K. KIRK

*Attesting Officer*     Acting Commissioner of Patents and Trademarks